(12) United States Patent
Phan et al.

(10) Patent No.: US 8,496,473 B2
(45) Date of Patent: Jul. 30, 2013

(54) SYSTEMS AND METHODS FOR FABRICATING A DENTAL TEMPLATE

(75) Inventors: Loc X. Phan, San Jose, CA (US); Peter G. Knopp, Palo Alto, CA (US); Eric Kuo, Foster City, CA (US); Amir Abolfathi, Menlo Park, CA (US); Huafeng Wen, Redwood Shores, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 11/297,129

(22) Filed: Dec. 7, 2005

(65) Prior Publication Data
US 2006/0084030 A1 Apr. 20, 2006

Related U.S. Application Data

(63) Continuation of application No. 10/870,808, filed on Jun. 17, 2004, now Pat. No. 7,056,115, which is a continuation of application No. 10/375,223, filed on Feb. 26, 2003, now abandoned.

(51) Int. Cl.
*A61C 3/00* (2006.01)
*B21F 43/00* (2006.01)

(52) U.S. Cl.
USPC ......................................... 433/24; 29/896.11

(58) Field of Classification Search
USPC ............. 433/29, 6–24, 3–5, 72–74, 215–225; 29/896.1, 896.11; 128/859
See application file for complete search history.

(56) References Cited

U.S. PATENT DOCUMENTS

| | | | | |
|---|---|---|---|---|
| 3,848,335 A * | 11/1974 | Bergersen | ........................... | 433/6 |
| 3,949,478 A * | 4/1976 | Schinhammer | .................... | 433/3 |
| 4,183,141 A * | 1/1980 | Dellinger et al. | .................. | 433/3 |
| 4,360,341 A * | 11/1982 | Dellinger | ........................ | 433/24 |
| 4,501,554 A * | 2/1985 | Hickham | ........................ | 433/24 |
| 4,526,540 A * | 7/1985 | Dellinger | ........................ | 433/24 |
| 4,551,096 A * | 11/1985 | Dellinger | ........................ | 433/24 |
| 4,657,508 A * | 4/1987 | Dellinger | ........................ | 433/24 |
| 5,055,039 A * | 10/1991 | Abbatte et al. | ................... | 433/24 |
| 5,791,896 A * | 8/1998 | Ipenburg | .......................... | 433/3 |
| 5,971,754 A * | 10/1999 | Sondhi et al. | .................... | 433/24 |
| 6,086,855 A * | 7/2000 | Fischer | .......................... | 424/49 |
| 6,123,544 A * | 9/2000 | Cleary | .......................... | 433/24 |
| 6,183,248 B1 * | 2/2001 | Chishti et al. | ...................... | 433/6 |
| 6,554,613 B1 | 4/2003 | Sachdeva et al. | | |
| 6,905,337 B1 | 6/2005 | Sachdeva | | |
| 6,918,761 B2 | 7/2005 | Sachdeva et al. | | |
| 2002/0010568 A1 * | 1/2002 | Rubbert et al. | ................... | 703/6 |
| 2004/0175670 A1 | 9/2004 | Kopelman et al. | | |
| 2005/0074716 A1 | 4/2005 | Cleary et al. | | |
| 2005/0208450 A1 | 9/2005 | Sachdeva et al. | | |
| 2005/0239013 A1 | 10/2005 | Sachdeva | | |

* cited by examiner

*Primary Examiner* — Yogesh Patel
(74) *Attorney, Agent, or Firm* — Wilson Sonsini Goodrich & Rosati

(57) ABSTRACT

A dental template to position an object on a patient's tooth includes digitizing the patient's tooth; adding virtual objects to predetermined locations on the digitized tooth; and fabricating the dental template to locate the object on the patient's tooth. The template can be used for etching or for positioning brackets on teeth.

10 Claims, 5 Drawing Sheets

SYSTEMS AND METHODS FOR FABRICATING A DENTAL TEMPLATE

CROSS-REFERENCE TO RELATED APPLICATIONS

The present application is a continuation of U.S. application Ser. No. 10/870,808 filed Jun. 17, 2004 now U.S. Pat. No. 7,056,115, which is a continuation of U.S. application Ser. No. 10/375,223, filed Feb. 26, 2003 now abandoned, the full disclosures of which are incorporated herein by reference.

BACKGROUND

The present invention relates generally to the field of orthodontics.

One objective in orthodontics is to move a patient's teeth to a position where the teeth function optimally and are also aesthetically pleasing. Conventional appliances such as braces and wires can be positioned on a patient's teeth by a treatment provider such as an orthodontist or a suitably trained dentist. Once mounted on the teeth, the hardware exerts continual forces on the teeth and gradually urges the teeth toward their ideal positions. Over a period of time, the treatment provider adjusts the braces and the wires to move the teeth toward their final destination.

Orthodontic brackets are often bonded directly to the patient's teeth. Typically, a small quantity of adhesive is placed on the base of each bracket and the bracket is then placed on a selected tooth. Before the adhesive is set, the bracket is maneuvered to a desired location on the tooth. Once the adhesive has hardened, the bracket is bonded to the tooth with sufficient strength to withstand subsequent orthodontic forces as treatment progresses. One shortcoming with this technique is the difficulty in accessing the optimal surface for bracket placement on severely crowded teeth or in teeth where the bonding surface is obstructed by teeth in the opposing arch during jaw closure. With posterior teeth, the treatment provider may have difficulty seeing the precise position of the bracket relative to the tooth surface. The amount of time needed to carry out the bonding procedure may be a nuisance both to the patient as well as to the treatment provider. Also, the necessity of minimizing moisture contamination from the patient's saliva can prolong the procedure and also unduly impair the accuracy of placement of the brackets on the teeth. All of these factors increase the chance that the ultimate adhesive bond will not have sufficient strength to retain the brackets on the teeth during treatment. One way to overcome some of the limitations of direct bracket placement is with indirect bonding. Typically, an impression of each of the patient's dental arches is taken and a replica plaster or "stone" model is made from each impression and sealed. Brackets are bonded to the sealed stone models using a temporary cement. A transfer tray is then made by placing matrix material over both the model and the brackets on the model. For example, a heated plastic sheet matrix material may be placed over the model and brackets and then under pressure. The plastic sheet material then assumes a configuration that precisely matches the shape of the replica teeth of the stone model with the brackets in the desired position. The plastic material is then allowed to cool and harden to form a tray. The temporary adhesive is removed, and permanent adhesive is placed on the base of each bracket in the tray, and the tray with the embedded brackets then placed over matching portions of the patient's dental arches. Since the configuration of the interior surface of the tray closely matches the respective portions of the patient's dental arches, each bracket is ultimately positioned on the patient's teeth at precisely the same location that corresponds to the previous location of the same bracket on the stone model. The adhesive is hardened and the matrix material removed, leaving the brackets in the desired positions. This method however, is labor intensive. An additional problem with the indirect method is that brackets may become dislodged during the removal of the matrix from the dental arches. The problem of proper access to tooth surfaces for optimal placement in the event of severely crooked teeth or teeth which interfere with the opposing arch such that brackets cannot be placed is also not addressed.

New methods such as those described in U.S. Pat. No. 5,975,893, commonly assigned to the assignee of the instant invention, allow the treatment to be planned in advance and a plurality of polymeric shell appliances are fabricated at the outset of treatment. The use of polymeric shell appliances provides treatments that are more comfortable; less visible, and removable by the patient, and greatly improves patient compliance, comfort, and satisfaction.

Since each patient is unique and requires customized treatment, on occasion, a patient may need to utilize a combination of braces/wires and shell appliances. Ideally, a device would enable precise placement of brackets on teeth with minimal risk of displacing the brackets upon removal of the matrix and allow final placement to be independent of adjacent geometries. In other words, placement of obscured tooth surfaces may be accomplished at a later time when the tooth surfaces have been exposed through initial uncrowding of severely overlapped teeth.

SUMMARY

A dental template is disclosed to support positioning an object on a patient's tooth oriented in such a way that all the objects as a whole are lined up to a user defined ideal arrangement. Also, a method is disclosed for fabricating the template. The method includes digitizing the patient's teeth; adding virtual objects to predetermined locations on the digitized teeth; and fabricating the dental template to locate the object on the patient's teeth.

Advantages of the template may include one or more of the following. The template can be used for etching or for positioning brackets on teeth. The treatment can be done virtually and the placement of the brackets can be done using a template device that is a removable guide. This device allows precise placement of the bracket and enables bracket placement onto specific teeth independent of overall arch geometry. The template makes it easier for a less well-trained or an untrained person to bond a bracket. The system minimizes variations in the perception of distance and angles. The template provides a very precise control on the placement of the bracket. Since bracket placement is one of the critical variables to successful treatment, the template improves treatment precision from patient to patient and from tooth to tooth.

The device itself may not necessarily contain the bracket as with traditional indirect bonding (IDB) templates, but rather, directs the user as to the precise location where the bracket should be placed based on geometric fit.

DESCRIPTION

Figure 1:
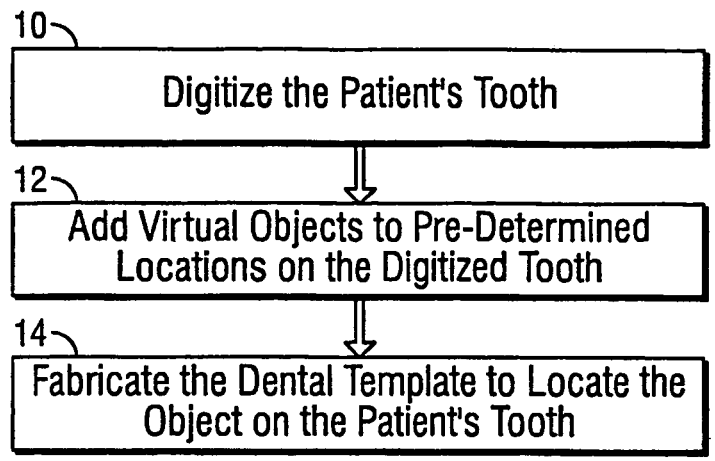
FIG. 1 shows an exemplary method or process to fabricate a dental template to position an object on a patient's tooth.

FIG. 1 shows an exemplary method or process to fabricate a dental template to position an object on a patient's tooth. First, the process digitizes the patient's tooth (10). Next, virtual objects are added to pre-determined locations on the digitized tooth (12). Finally, the process fabricates the dental template to locate the object on the patient's tooth (14). One detailed implementation of FIG. 1 is described in FIGS. 3A and 3B below.

Figure 2A:
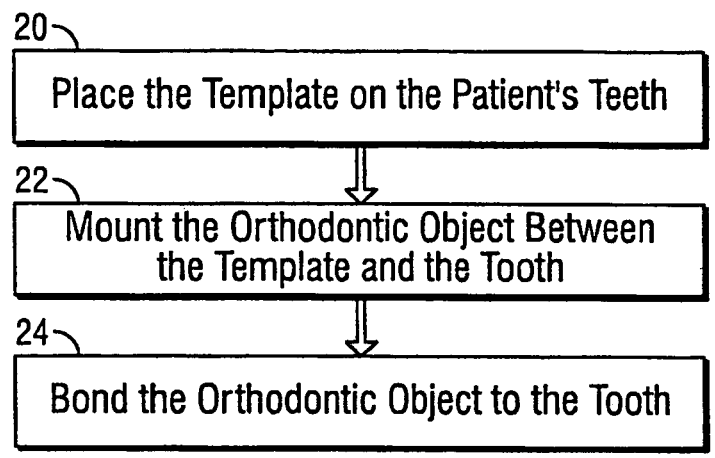
FIG. 2A shows an exemplary method or process for placing an orthodontic object on a patient's tooth.

FIG. 2A shows an exemplary method or process for placing an orthodontic object on a patient's tooth. The process uses the template fabricated in the process of FIG. 1. The process includes placing the template on the patient's teeth (20); mounting the orthodontic object between the template and the tooth (22); and bonding the orthodontic object to the tooth (24). In the bonding operation, chemical curing or light curing adhesives can be used. In chemical curing, separately supplied curing components are mixed together and a small quantity of the mixture is placed on the back of the bracket prior to placing the bracket on the tooth. Light-curable adhesives include a photo-initiator that initiates the curing reaction once the adhesive is exposed to a sufficient amount of light. A common method of using light-curable adhesives for direct bonding includes the steps of placing a small quantity of the adhesive on the base of the bracket and then placing the bracket on the patient's tooth. The practitioner then shifts the bracket on the tooth as may be needed. Once the bracket is in its precise, intended location, light from a dental curing unit is directed toward the adhesive for a time period sufficient to satisfactorily cure the adhesive.

Figure 2B:
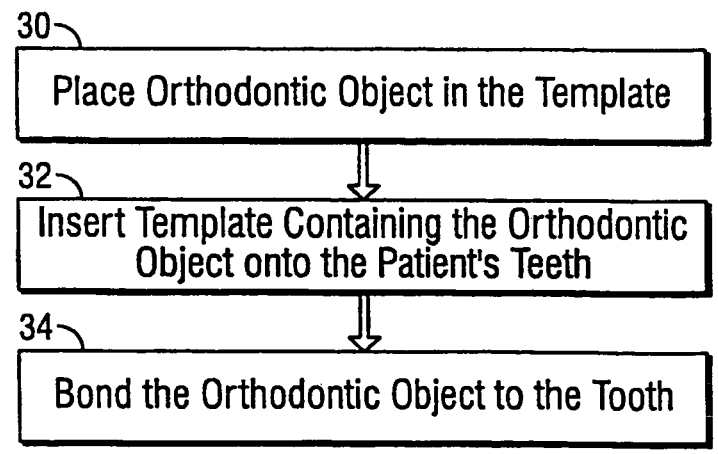
FIG. 2B shows a second method of placing the orthodontic object on a patient's tooth.

FIG. 2B shows a second method of placing the orthodontic object on a patient's tooth. In this process, the orthodontic object is placed in the template (30). Next, the process includes inserting the template containing the orthodontic object onto the patient's teeth (32). Finally, the process includes bonding the orthodontic object to the tooth (34).

Figure 3A:
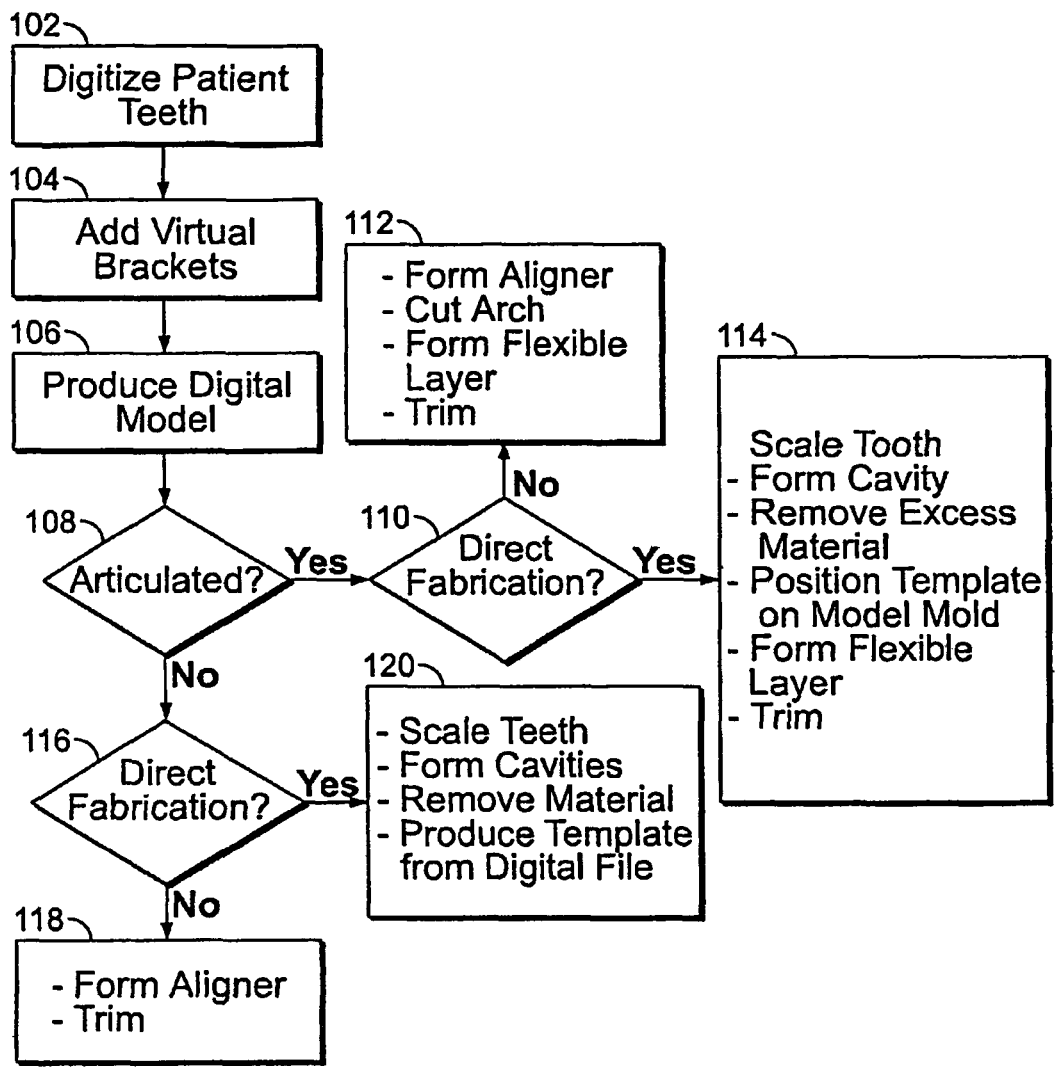
FIG. 3A illustrates an exemplary process for fabricating the dental template.

FIG. 3A illustrates an exemplary process for fabricating the dental template. First, a digital model of a patient's teeth of a patient is obtained (102). The digital model can be obtained in a variety of ways. For example, the patient's teeth may be scanned or imaged using well known technology, such as X-rays, three-dimensional x-rays, computer-aided tomographic images or data sets, magnetic resonance images, etc. There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

Next, virtual brackets are selected (104). The virtual brackets are 3D models of existing brackets. The 3D models may be a computer aided design (CAD) model or may be scanned using scanners described above. The brackets may be positioned on a digitized tooth using a computer or workstation having a suitable graphical user interface (GUI) and software appropriate for viewing and modifying the images. The above-described component identification and component manipulation software is designed to operate at sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intra-oral physiology and teeth-moving dynamics, can simply use the component identification and manipulation software as a tool and disable or otherwise ignore the advice.

While the methods will rely on computer manipulation of digital data, the dental templates or appliance may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare the template using pressure and vacuum molding techniques. While such manual creation of the appliance systems of the present invention will generally be much less preferred, systems so produced will come within the scope of the present invention.

Using the CAD workstation, a combined digital model of the virtual brackets and the teeth is produced (106).

In one implementation, four template embodiments can be selected: Direct-Articulated, Indirect-Articulated, Direct-Unified, and Indirect-Unified, as discussed in more detail in FIG. 3B.

Once the template has been fabricated, in one embodiment, the system sets the template over the model of the patient's arches or otherwise positions the template in the approximate locations of their respective teeth. A thermoformed, cast, or otherwise formed layer of flexible material is deposited on the bodies. The layer makes intimate and relatively durable contact with the bodies of the templates. This may be accomplished, among other ways, by adding or subtracting geometries to the bodies to engage well with the material layer. This method could be performed either by a factory or in the orthodontist's office.

The system produces both the template bodies and the inter-tooth portion(s) at the same time and subsequently alter the stiffness of the various parts. One way of achieving this would be to produce the entire arch with a 3-D printer, mask the tooth bodies from the inter-tooth portions, embed the tooth bodies with a rigidifying agent and the inter-tooth portions with an agent to create flexibility.

From 110, if a directly formed template is produced, the process proceeds to 114 where each tooth is scaled; a cavity is formed to enclose the tooth when the dental template or appliance is inserted over the patient's teeth. Next, unnecessary structures are removed from the digital model. The digital model is produced as a physical model. A flexible pliable layer is formed and the resulting combination is trimmed to allow proper fit and function.

Alternatively, from 110 if indirect forming is to be done, the process forms and aligner, and cuts and removes excess material (112).

From 108, for direct fabrication of a template of a whole arch (116) using an indirectly-produced template, the process forms an aligner, cuts and removes excess material (118). In the case of a directly formed whole arch template (116), the process proceeds to 120 where the entire arch is scaled; a cavity is formed to enclose the arch when the dental template or appliance is inserted over the patient's teeth. Next, unnecessary structures are removed from the digital model. The digital model is produced as a physical model. A flexible pliable layer is formed and the resulting combination is trimmed to allow proper fit and function.

Figure 3B:
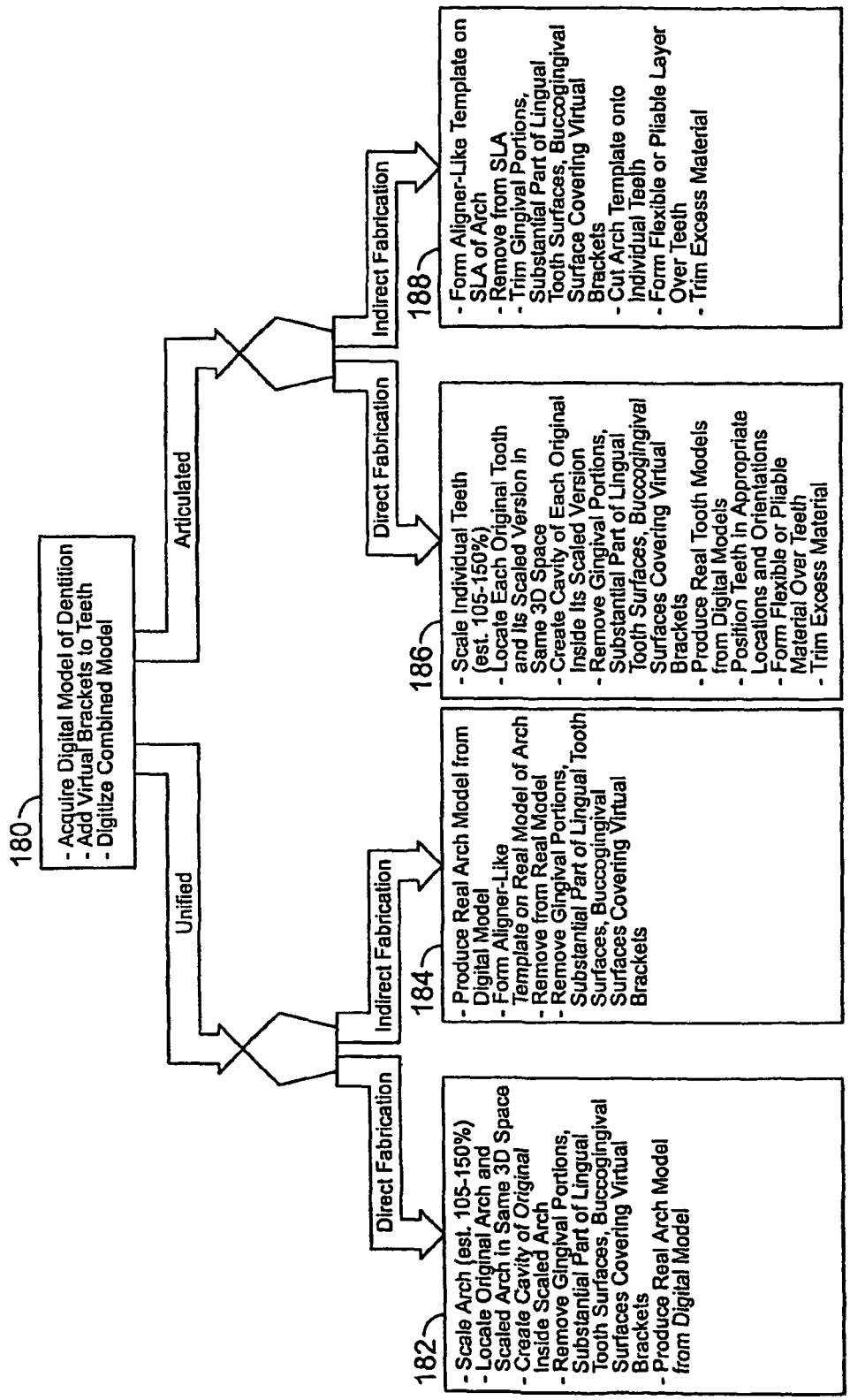
FIG. 3B shows a process for providing four possible templates.

FIG. 3B shows a process for providing four possible templates. First, the process acquires a digital model of dentition, adds virtual brackets to teeth, and creates a combined model (180). Next, one of four templates options can be selected. The first option is unified (or single piece)—direct bonding option where the process scales the arch (est. 105-150%), locates original arch and scaled arch in same 3D space, creates cavity of original inside scaled arch, removes gingival portions, substantial part of lingual tooth surfaces, buccogingival surfaces covering virtual brackets, and produces real arch model from digital model (182).

In the second option (unified indirect bonding), the process produces real arch model from digital model and forms a removable appliance (aligner) template on real model of arch. The template is removed from the real model, and the process then removes gingival portions, substantial part of lingual tooth surfaces, buccogingival surfaces covering virtual brackets (184).

In the third option (articulated direct bonding), the process scales individual tooth (est. 105-150%), locates each original tooth and its scaled version in same 3D space, creates a cavity of each original inside its scaled version, removes gingival portions, substantial part of lingual tooth surfaces, buccogingival surfaces covering virtual brackets, produces real tooth models from digital models, positions teeth in appropriate locations and orientations, forms a flexible or pliable material over teeth, and trims excess material from the template (186).

In the fourth option (articulated indirect bonding), the process forms an aligner-like template on a mold of an arch. The template is removed from the mold and gingival portions, substantial part of lingual tooth surfaces and buccogingival surface covering virtual brackets are trimmed. The process cuts an arch template onto an individual tooth. A flexible or pliable layer over the template is formed, and excess material is trimmed (188).

In yet another embodiment, a process obtains tooth geometries. If direct bonding is to be used, the process performs the following:
  Scale the arch to a value likely within the range 105-150%.
  Co-locate the original (100%) arch and the scaled arch in the same 3D space
  Place a virtual bracket or other appropriate geometry at a specific location and in a specific orientation on each tooth to be treated.
  Cavity the original arch and the brackets in the scaled arch.
  Remove from the resulting template or body those aspects that would be below the gingival line. Remove the portions of the resultant body buccal and gingival to the brackets remove a substantial portion or all of the lingual aspect of the resultant body.
  Convert this computer model to a real part, likely through the use of a rapid prototyping method (e.g. Fused Deposition Modeling, 3-D Printing, stereolithography).

If indirect bonding is to be done, the following operations are done using an arch model:
  Form an Aligner-like appliance or template over an arch model that has brackets or other appropriate geometries properly located on the teeth.
  Remove from the Aligner or template those aspects that would be below the gingival line or in direct interproximal contact with adjacent teeth. Remove the portions of the Aligner buccal and gingival to the bracket. Remove a substantial portion or all of the lingual aspect of the Aligner.

After completion, the process ships the templates, bodies or the completed appliance to the orthodontist either at the onset of treatment or when it is requested.

Figure 4A:
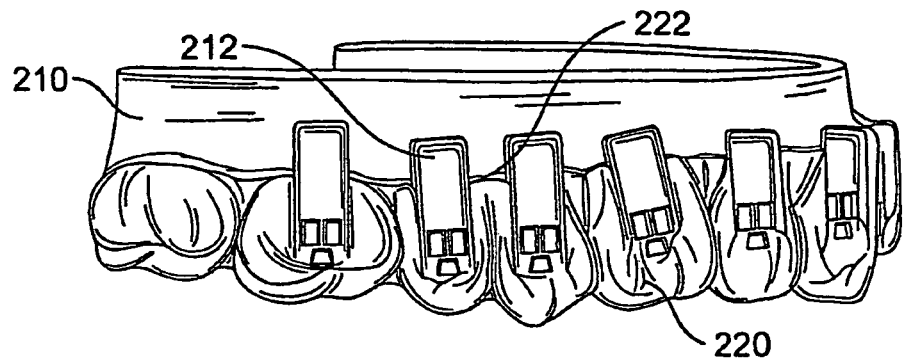
FIGS. 4A-4D show perspective views of various templates.

FIG. 4A shows one embodiment of a dental template 220 or appliance formed over a mold 210. The template looks like a removable appliance; however, it has openings 222 or "portholes" approximating the footprint, key portions of the footprint, and/or possibly other geometrical features of a bracket to guide the precise placement of the bracket on its respective tooth. The template 220 with the openings 222 or "portholes" may also be a guide for enamel etching or adhesive placement.

The mold 210 is a physical rendition of a digital model that has been fabricated using rapid prototyping methods. A bump or projection 212 rises from the mold 210 so when the dental template or appliance is thermal-formed, an opening 222 is formed on the template 220. The opening 222 is where the template is cut out along the edge of the bump or projection 212. The opening 222 has a bracket support edge 226, whose operation is described in more detail in FIG. 4B. In addition to the support edge 226, the template 220 may have features that will minimize the retention of it on the dental anatomy. For example, the lingual side of the device may not have maximum coverage.

Fabrication methods for the mold 210 employ a rapid prototyping device such as a stereolithography machine or a fused deposition modeling machine. A suitable rapid prototyping machine is Model SLA-250/50 available from 3D System, Valencia, Calif. The rapid prototyping machine selectively hardens a liquid or other non-hardened resin into a three-dimensional structure, which can be separated from the remaining non-hardened resin, washed, and used either directly as the appliance or indirectly as a mold for producing the appliance. The prototyping machine receives the individual digital data sets and produces one structure corresponding to each of the desired appliances. Generally, because the stereolithography machine may utilize a resin having non-optimum mechanical properties and which may not be generally acceptable for patient use, the prototyping machine produces the mold 210. After the positive model is prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine produces each of the appliances directly from the positive tooth model and the desired material. Suitable vacuum molding machines are available from Raintree Essix, Inc.

In one embodiment, the template is made from a thick material (for example 0.03 inches or more) to provide the user with more guidance in the depth direction. Furthermore, the thick template allows easier lining the bracket to the tooth.

More information on the fabrication of the dental template or appliance is disclosed in U.S. Pat. No. 6,499,997 "Manipulable dental model system for fabrication of a dental appliance"; U.S. Pat. No. 6,497,574 "Modified tooth positioning appliances and methods and systems for their manufacture"; U.S. Pat. No. 6,488,499 "Methods for correcting deviations in preplanned tooth rearrangements"; U.S. Pat. No. 6,485,298 "System and method for releasing tooth positioning appliances"; U.S. Pat. No. 6,471,511 "Defining tooth-moving appliances computationally"; U.S. Pat. No. 6,463,344 "Efficient data representation of teeth model"; U.S. Pat. No. 6,457,972 "System for determining final position of teeth"; U.S. Pat. No. 6,454,565 "Systems and methods for varying elastic modulus appliances"; U.S. Pat. No. 6,450,807 "System and method for positioning teeth"; U.S. Pat. No. 6,409,504 "Manipulating a digital dentition model to form models of individual dentition components"; U.S. Pat. No. 6,406,292 "System for determining final position of teeth"; U.S. Pat. No. 6,398,548 "Method and system for incrementally moving teeth"; U.S. Pat. No. 6,394,801 "Manipulable dental model system for fabrication of dental appliances"; U.S. Pat. No. 6,390,812 "System and method for releasing tooth positioning appliances"; U.S. Pat. No. 6,386,878 "Systems and methods for removing gingiva from teeth"; U.S. Pat. No. 6,386,864 "Stress indicators for tooth positioning appliances"; U.S. Pat. No. 6,371,761 "Flexible plane for separating teeth models"; U.S. Pat. No. 6,318,994 "Tooth path treatment plan"; U.S. Pat. No. 6,309,215 "Attachment devices and method for a dental appliance"; U.S. Pat. No. 6,299,440 "System and method for producing tooth movement"; U.S. Pat. No. 6,227,851 "Manipulable dental model system for fabrication of a dental appliance"; U.S. Pat. No. 6,227,850 "Teeth viewing system"; U.S. Pat. No. 6,217,325 "Method and system for incrementally moving teeth"; U.S. Pat. No. 6,210,162 "Creating a positive mold of a patient's dentition for use in forming an orthodontic appliance"; and U.S. Pat. No. 5,975,893 "Method and system for incrementally moving teeth," the contents of which are hereby incorporated by reference.

Figure 4B:
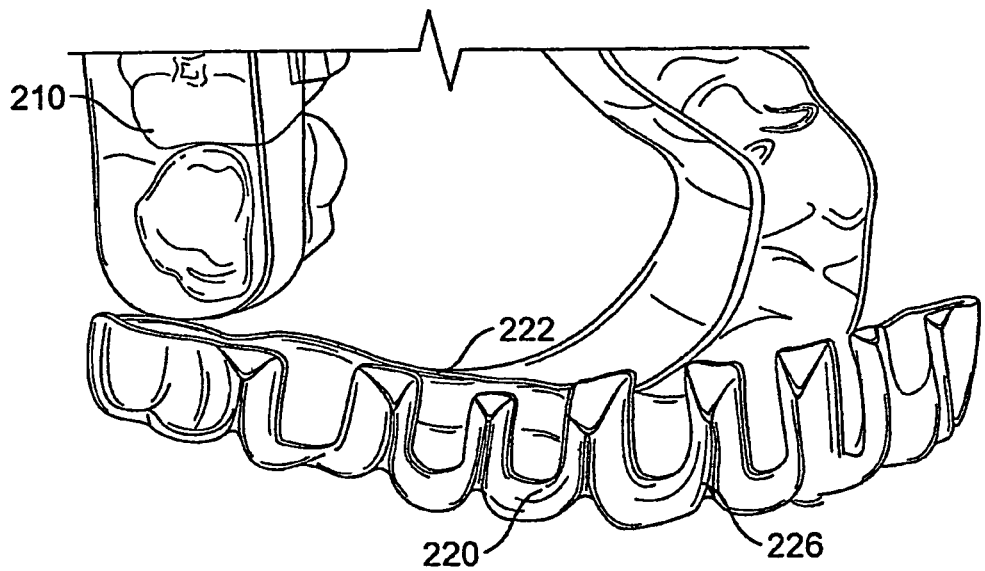

Turning now to FIG. 4B, the template 220 is separated from the mold 210. The opening 222 allows a bracket base to fit into the opening 222. Bracket support edge 226 is needed to securely position the bracket in the template 220. In this embodiment, the bracket support edge 226 is curvaceous. If the edge 226 had been terminated as a simple flat edge, the bracket can be located in X and Y surfaces on the tooth, but the Z direction (buccal lingual direction) would not be controlled. The edge 226 provides the needed control of the bracket's degree of freedom in the Z direction to allow orientation of the bracket about any given axis. Those features allow the bracket to be secured in the proper position and orientation on its respective tooth. The edge 226 can change, depending on vendor-to-vendor or prescription-to-prescription.

Another embodiment of the template can be used for etching bonding chemicals on the patient's teeth. The etching template directs the user to predetermined locations on the teeth surfaces that need to be bonded. The etching template can be either the format of a windowed template or a concave surfaced template where bonding gel is loaded or pre-loaded into the concavity.

Figure 4C:
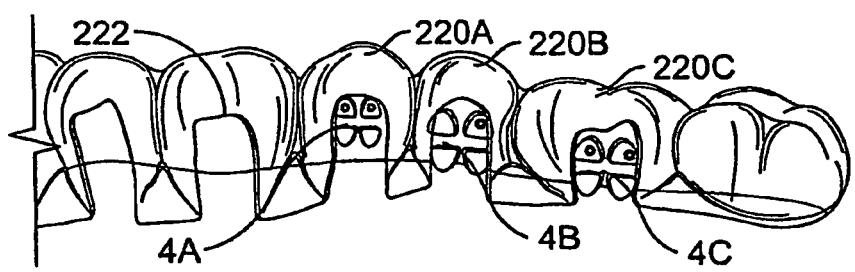

FIG. 4C shows a template wherein each of the openings, cut-outs, port-holes, or slots 222 in the template 220 are designed to fit particular brackets 4A, 4B and a 4C, each of which fits into its respective portion on the template.

Figure 4D:
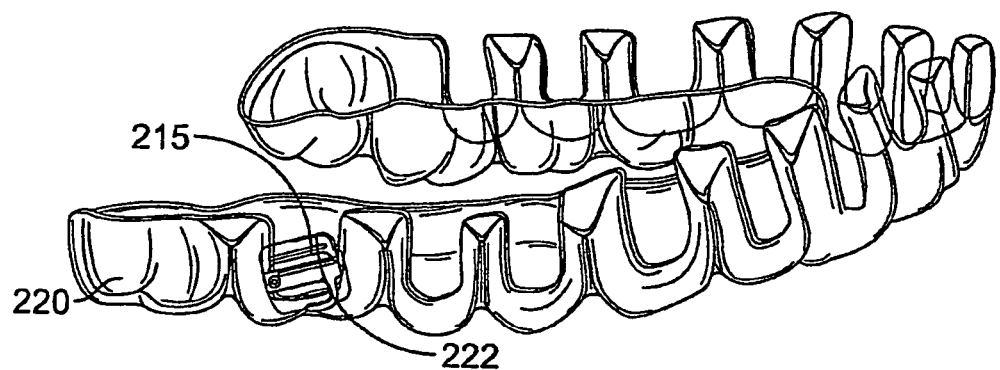

FIG. 4D shows that the system is not limited to bracket design or shape. In FIG. 4D, a molar tube bracket 215 can be placed on the opening 222. Hence, the template 220 is not limited to any specific bracket. Rather, any form of fixed orthodontic appliances placed on a tooth could be accommodated.

Figure 5A:
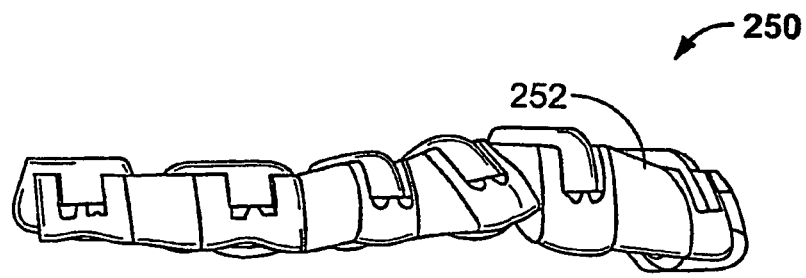
FIGS. 5A and 5B illustrate two embodiments of articulated templates.
Figure 5B:
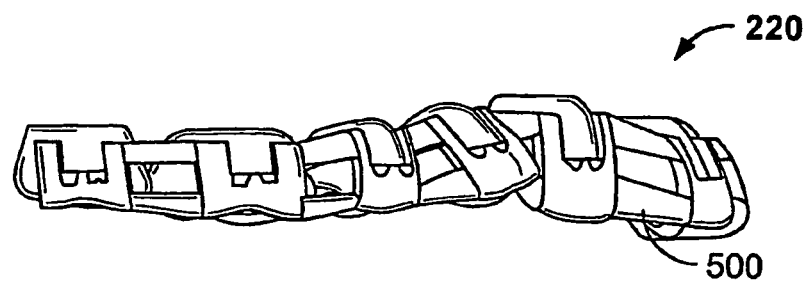

FIGS. 5A and 5B illustrate two exemplary embodiments of articulated templates. FIG. 5A shows two segments joined at the interproximal regions of two adjacent teeth. A number of alternate methods to join the teeth can be used, including that the joining methods could be alternate or vary from one interproximal region to the next. Further, the joining method could also be a layer or layers that cover additional or different surfaces of the teeth as depicted in FIG. 5B.

In FIG. 5A, the template is made up of a number of movable template components 250. Each of the template components 250 can be mounted on a patient's tooth to facilitate bracket bonding. The movable template components 250 are physically linked together by a sheet of material 252 deposited above the components 250 so that they do not break-up or otherwise become disassembled upon removal from its mold or stereolithography apparatus (SLA) model. The articulated templates are advantageous in that they provide greater adjustment flexibility.

The template can additionally be used as an etching template. An etching template allows the doctor to precisely etch the areas of the teeth on which the brackets will be placed. The small windows bound the regions that will be etched to minimize teeth sensitivity to etching or unwanted enamel removal. In another version of the etching template, the cut outs would not be formed. Instead those areas would be concavities facing the tooth surfaces. These concavities would contain an etching compound. The user would expose or activate the etching compound prior to setting the template on the teeth.

The template 220 may be made from materials that contain physical property switches for ease of removal. These switches might include temperature responsive, pH responsive, moisture responsive or a multi-layer system wherein the layers have varying physical properties. The section 500 represents a flexible or pliable material. Additionally, the material could be fiber, cord, fiber mesh, or a fiber-reinforced solid. The interproximal material can be homogenous or heterogeneous.

Various alternatives, modifications, and equivalents may be used in lieu of the above components. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner. Further, while the invention has been shown and described with reference to an embodiment thereof, those skilled in the art will understand that the above and other changes in form and detail may be made without departing from the spirit and scope of the following claims.

What is claimed is:

1. A template for positioning an orthodontic object on teeth of a patient, comprising:
 a template adapted to fit on each of a plurality of the teeth;
  said template comprising an inner surface adapted to be positioned adjacent to the patient's teeth and an outer surface displaced away from the inner surface, the inner surface defining a plurality of tooth receiving cavities, each cavity shaped based on a non-scaled version of a digital tooth model of the patient made using a computerized system to match adjacent surfaces of a received tooth such that each received tooth geometrically fits within each cavity, wherein the outer surface of the template is shaped based on a larger digitally scaled version of the digital tooth model such that the outer surface of the template is larger than the patient's tooth and matching outer surface of the teeth; and
  the template further comprising multiple openings on a gingival side of the template, each opening shaped to allow a base of the orthodontic object to fit directly into the opening to position the orthodontic object in the template and to guide the orthodontic object into a target position on one of the patient's teeth.

2. The template of claim 1, wherein a thickness of the template is at least 0.03 inches in a buccal-lingual direction.

3. The template of claim 1, wherein the template is made from a variable physical property material such that the appliance has a first state for retention of the template on the patient's teeth and a second state for facilitating removal of the appliance from the patient's teeth.

4. The template of claim 1, wherein the template is articulated.

5. The template of claim 1, wherein the template is unified.

6. The template of claim 1, wherein the outer surface comprises a larger scaled version of the inner surface that is between about 105% to about 150% of the inner surface.

7. The template of claim 1, wherein the at least one opening comprises a rounded edge for positioning of a bracket.

8. A template for positioning an orthodontic object on teeth of a patient, comprising:
 a template adapted for placement over the teeth so as to fit on and span a plurality of teeth in a dental arch of the patient, the template comprising an inner surface adapted to be positioned adjacent to the patient's teeth and an outer surface displaced away from the inner surface,
 the inner surface defining a plurality of tooth receiving cavities, each cavity shaped based on a non-scaled version of a digital tooth model of the patient made using a computerized system to match adjacent surfaces of a received tooth such that each received tooth geometrically fits within each cavity, wherein
 the outer surface of the template is shaped based on a larger digitally scaled version of the digital tooth model, such that the outer surface of the template is larger than the patient's tooth and matching outer surface of the teeth,
 the template further comprising one or more openings on a gingival side of the template, shaped to guide the orthodontic object into a target position on one of the patient's teeth, wherein the template is formed by a process comprising: generating a template model based on the digital model; and generating the template based on the template model.

9. The template of claim 8, wherein the opening of the template is configured such that a bracket for placement on the patient's tooth is positionable in the opening and the bracket is movable through the opening to the gingival side during removal of the template from the patient's teeth.

10. A template for positioning an orthodontic object on teeth of a patient, comprising:
 a template adapted for placement over the teeth so as to fit on and span a plurality of the patient's teeth, the template comprising an inner surface adapted to be positioned adjacent to the patient's teeth and an outer surface displaced away from the inner surface,
 the inner surface defining a plurality of tooth receiving cavities, each cavity shaped to match adjacent surfaces of the tooth such that each received tooth geometrically fits within the each cavity, wherein
 the outer surface of the template is shaped based on a larger digitally scaled version of a digital tooth model made using a computerized system, such that the outer surface of the template is larger than the patient's tooth and matching outer surface of the teeth,
 the template further comprising a plurality of openings each configured to directly receive and guide the object into a target position on a different one of the patient's teeth, the openings comprising a cut-out that is open to a gingival side of the template and an object support edge shaped to allow an object base to fit directly into the opening to position the template.

* * * * *